United States Patent
Shikama et al.

(10) Patent No.: US 11,607,195 B2
(45) Date of Patent: Mar. 21, 2023

(54) ULTRASOUND DIAGNOSIS APPARATUS, STORAGE MEDIUM, AND METHOD FOR SETTING OF ATTENUATION CORRECTION

(71) Applicant: Konica Minolta, Inc., Tokyo (JP)

(72) Inventors: Jo Shikama, Machida (JP); Takashi Kimoto, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 622 days.

(21) Appl. No.: 16/231,784

(22) Filed: Dec. 24, 2018

(65) Prior Publication Data
US 2019/0216434 A1 Jul. 18, 2019

(30) Foreign Application Priority Data
Jan. 18, 2018 (JP) .............................. JP2018-006065

(51) Int. Cl.
*A61B 8/08* (2006.01)
*G01S 7/52* (2006.01)
*A61B 8/00* (2006.01)
*G06T 5/50* (2006.01)

(52) U.S. Cl.
CPC ............ *A61B 8/5207* (2013.01); *A61B 8/461* (2013.01); *A61B 8/5269* (2013.01); *G01S 7/52033* (2013.01); *G06T 5/50* (2013.01); *A61B 8/467* (2013.01); *G06T 2207/10132* (2013.01)

(58) Field of Classification Search
CPC ..................... A61B 8/5207; G06T 2207/10132
See application file for complete search history.

(56) References Cited

U.S. PATENT DOCUMENTS

| | | | | |
|---|---|---|---|---|
| 2003/0187353 A1* | 10/2003 | Ng | ...................... | G01S 7/52063 600/437 |
| 2013/0249842 A1* | 9/2013 | Varna | .................. | G06F 3/04886 345/173 |
| 2015/0196277 A1* | 7/2015 | Yang | ..................... | A61B 8/5207 600/437 |

FOREIGN PATENT DOCUMENTS

JP 2006296978 A 11/2006

* cited by examiner

*Primary Examiner* — Jason M Ip
(74) *Attorney, Agent, or Firm* — Lucas & Mercanti, LLP

(57) ABSTRACT

An ultrasound diagnosis apparatus includes: a hardware processor which performs control of causing a display to display an ultrasound image subjected to attenuation correction, based on a received signal and setting of the attenuation correction, the attenuation correction correcting strength of the received signal lowered due to attenuation of ultrasound waves inside a subject based on a correction amount according to a reflection depth of the ultrasound waves inside the subject; and an input receiver which receives an input operation that designates an adjustment amount, wherein the hardware processor changes the setting of the attenuation correction based on the adjustment amount, and in the changing the setting of the attenuation correction, sets the correction amount, for each of different reflection depths, to an amount according to a product of the adjustment amount and a predetermined weighting factor, the predetermined weighting factor being set correspondingly to each of the reflection depths.

13 Claims, 9 Drawing Sheets

| DEPTH SEGMENT | WEIGHTING FACTOR | |
|---|---|---|
| | ROTATION INPUT KEY 51 | ROTATION INPUT KEY 52 |
| D1 | 10 | 0 |
| D2 | 9 | 1 |
| D3 | 8 | 2 |
| D4 | 6 | 4 |
| D5 | 4 | 6 |
| D6 | 2 | 8 |
| D7 | 1 | 9 |
| D8 | 0 | 10 |

| DEPTH SEGMENT | WEIGHTING FACTORS FOR ROTATION INPUT KEY 51 | | | |
|---|---|---|---|---|
| | DEPTH SETTING A | DEPTH SETTING B | DEPTH SETTING C | ... |
| D1 | 10 | 10 | 10 | ... |
| D2 | 9 | 9 | 8 | ... |
| D3 | 8 | 8 | 6 | ... |
| D4 | 6 | 6 | 4 | ... |
| D5 | 4 | 4 | 1 | ... |
| D6 | 2 | 1 | 0 | ... |
| D7 | 1 | 0 | 0 | ... |
| D8 | 0 | 0 | 0 | ... |

In

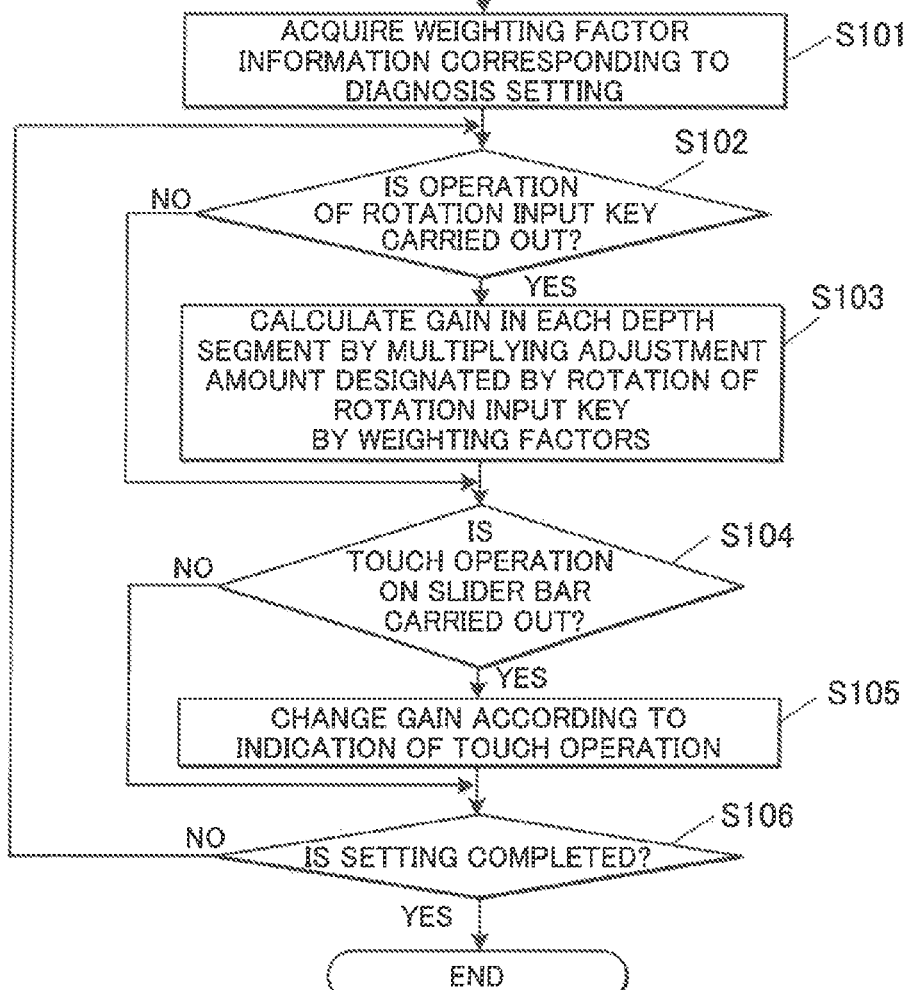
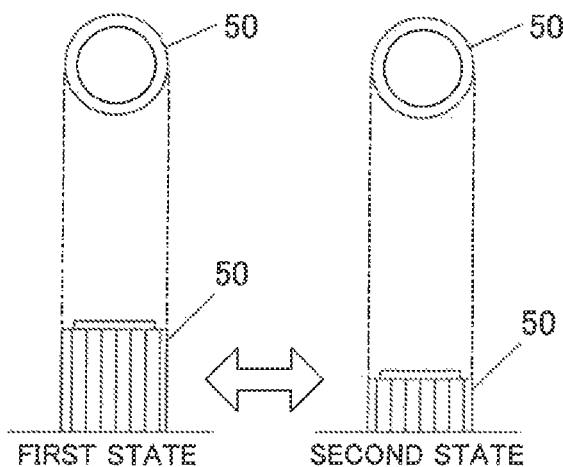

| DEPTH SEGMENT | WEIGHTING FACTOR | | | | | | | |
|---|---|---|---|---|---|---|---|---|
| | ROTATION INPUT KEY 541 | ROTATION INPUT KEY 542 | ROTATION INPUT KEY 543 | ROTATION INPUT KEY 544 | ROTATION INPUT KEY 545 | ROTATION INPUT KEY 546 | ROTATION INPUT KEY 547 | ROTATION INPUT KEY 548 |
| D1 | 10 | 9 | 8 | 6 | 4 | 1 | 0 | 0 |
| D2 | 9 | 10 | 9 | 8 | 6 | 4 | 1 | 0 |
| D3 | 8 | 9 | 10 | 9 | 8 | 6 | 4 | 1 |
| D4 | 6 | 8 | 9 | 10 | 9 | 8 | 6 | 4 |
| D5 | 4 | 6 | 8 | 9 | 10 | 9 | 8 | 6 |
| D6 | 1 | 4 | 6 | 8 | 9 | 10 | 9 | 8 |
| D7 | 0 | 1 | 4 | 6 | 8 | 9 | 10 | 9 |
| D8 | 0 | 0 | 1 | 4 | 6 | 8 | 9 | 10 |

ULTRASOUND DIAGNOSIS APPARATUS, STORAGE MEDIUM, AND METHOD FOR SETTING OF ATTENUATION CORRECTION

BACKGROUND

Technical Field

The present invention relates to an ultrasound diagnosis apparatus, a storage medium, and a method for setting of attenuation correction.

Description of the Related Art

Conventionally, there is an ultrasound diagnosis apparatus which transmits ultrasound waves from an ultrasound probe into a subject, receives reflected waves of the ultrasound waves, generates an ultrasound image reflecting the internal structure of the subject by processing a received signal obtained from the reflected waves, and causes a display to display the ultrasound image. Such ultrasound diagnosis apparatuses are used for human medical care as noninvasive diagnosis apparatuses.

Ultrasound waves transmitted from an ultrasound probe attenuate as the ultrasound waves go deeper into a subject. Accordingly, the strength of a received signal obtained by receiving reflected waves of the ultrasound waves becomes lower as reflection depth, where the ultrasound waves are reflected, becomes greater (deeper). Therefore, from an ultrasound image in B mode, in which the strength of a received signal is converted into brightness for display, it is difficult to make an accurate diagnosis due to lowered visibility because the brightness is lower at portions where reflection depth is greater.

On the other hand, an attenuation correction technology is known, which corrects the strength of a received signal lowered due to attenuation of ultrasound waves by making the gain of the received signal larger as the reflection depth of ultrasound waves is greater (that is, time passing from transmission until reception is longer), so as to uniform brightness in an ultrasound image. This technology is also referred to as TGC (Time Gain Compensation), STC (Sensitivity Time Control), or the like.

Among such ultrasound diagnosis apparatuses capable of attenuation correction, some are configured to enable a user to individually adjust a gain in each depth segment when an ultrasound image is segmented in a depth direction into a plurality of depth segments. Common interfaces for such gain adjustment are a plurality of operation keys, such as slide switches or rotation input keys, for gain adjustment provided for the depth segments, respectively, which are operated individually. An ultrasound diagnosis apparatus provided with a touch panel on a display in place of such physical operation keys is also known. In such ultrasound diagnosis apparatus, a user can adjust a gain in each depth segment by carrying out a touch operation on an operation image for gain adjustment displayed on the display. For example, Japanese Patent Laid-Open No. 2006-296978 discloses a technology which causes a screen to display a coordinate area with a horizontal axis representing gain and a vertical axis representing reflection depth, and sets a gain in each depth segment based on the coordinates of a locus of touch drawn by using a finger or the like in the coordinate area.

SUMMARY

However, setting of attenuation correction by using a plurality of physical operation keys is complicated for users because it is necessary to individually operate the operation keys for a plurality of depth segments, respectively. In the technology disclosed in Japanese Patent Laid-Open No. 2006-296978, although setting of attenuation correction can be completed through a single touch operation that draws a locus of touch, it is not easy to draw a locus of touch in such a manner that a gain corresponding to each depth segment is accurately set as intended. If unintended setting is made, a touch operation is required again, which takes time and trouble.

As described above, the conventional technologies have the problem that it is difficult to easily make desired setting of attenuation correction.

Objects of the present invention are to provide an ultrasound diagnosis apparatus which makes it possible to more easily make desired setting of attenuation correction, as well as to provide a storage medium and a method for setting of attenuation correction.

To achieve at least one of the above-mentioned objects, an ultrasound diagnosis apparatus reflecting an aspect of the present invention is an ultrasound diagnosis apparatus which causes a display to display an ultrasound image based on a received signal, received by an ultrasound probe, of ultrasound waves that are transmitted by the ultrasound probe into a subject and reflected inside the subject, including:

a hardware processor which performs control of causing the display to display the ultrasound image subjected to attenuation correction, based on the received signal and setting of the attenuation correction, the attenuation correction correcting strength of the received signal lowered due to attenuation of the ultrasound waves inside the subject based on a correction amount according to a reflection depth of the ultrasound waves inside the subject; and an input receiver which receives an input operation that designates an adjustment amount related to the setting of the attenuation correction, wherein the hardware processor changes the setting of the attenuation correction based on the adjustment amount designated by the input operation, and in the changing the setting of the attenuation correction, sets the correction amount, for each of a plurality of the reflection depths that differ from each other, to an amount according to a product of the adjustment amount and a predetermined weighting factor, the predetermined weighting factor being set correspondingly to each of the plurality of reflection depths.

To achieve at least one of the above-mentioned objects, a non-transitory computer readable storage medium reflecting another aspect of the present invention stores a program causing a computer provided to an ultrasound diagnosis apparatus which causes a display to display an ultrasound image based on a received signal, received by an ultrasound probe, of ultrasound waves that are transmitted by the ultrasound probe into a subject and reflected inside the subject, to perform:

control of causing the display to display the ultrasound image subjected to attenuation correction, based on the received signal and setting of the attenuation correction, the attenuation correction correcting strength of the received signal lowered due to attenuation of the ultrasound waves inside the subject based on a correction amount according to a reflection depth of the ultrasound waves inside the subject;

changing the setting of the attenuation correction based on an adjustment amount related to the setting of the attenuation correction, the adjustment amount being designated by an input operation carried out on an input receiver; and in the changing the setting of the attenuation correction, setting the correction amount, for each of a plurality of the reflection depths that differ from each other, to an amount according to a product of the adjustment amount and a predetermined weighting factor, the predetermined weighting factor being set correspondingly to each of the plurality of reflection depths.

To achieve at least one of the above-mentioned objects, a method for setting of attenuation correction reflecting still another aspect of the present invention is a method for setting of attenuation correction in an ultrasound diagnosis apparatus which causes a display to display an ultrasound image based on a received signal, received by an ultrasound probe, of ultrasound waves that are transmitted by the ultrasound probe into a subject and reflected inside the subject, including:

causing the display to display the ultrasound image subjected to attenuation correction, based on the received signal and setting of the attenuation correction, the attenuation correction correcting strength of the received signal lowered due to attenuation of the ultrasound waves inside the subject based on a correction amount according to a reflection depth of the ultrasound waves inside the subject;

changing the setting of the attenuation correction based on an adjustment amount related to the setting of the attenuation correction, the adjustment amount being designated by an input operation carried out on an input receiver; and in the changing the setting of the attenuation correction, setting the correction amount, for each of a plurality of the reflection depths that differ from each other, to an amount according to a product of the adjustment amount and a predetermined weighting factor, the predetermined weighting factor being set correspondingly to each of the plurality of reflection depths.

BRIEF DESCRIPTION OF THE DRAWINGS

The advantages and features provided by one or more embodiments of the present invention will become more fully understood from the detailed description of embodiments given hereinbelow and the appended drawings, which are not intended as a definition of the limits of the present invention, wherein:

FIG. 5 shows an example of the contents of weighting factor data;

FIG. 6 shows another example of the contents of the weighting factor data;

FIG. 7 is a flowchart showing a control procedure of attenuation correction setting processing;

FIG. 8 shows a rotation input key according to modification 1;

DETAILED DESCRIPTION OF EMBODIMENTS

Hereinafter, one or more embodiments of an ultrasound diagnosis apparatus, a storage medium, and a method for setting of attenuation correction according to the present invention will be described with reference to the drawings. However, the scope of the present invention is not limited to the disclosed embodiments.

First Embodiment

Figure 1:
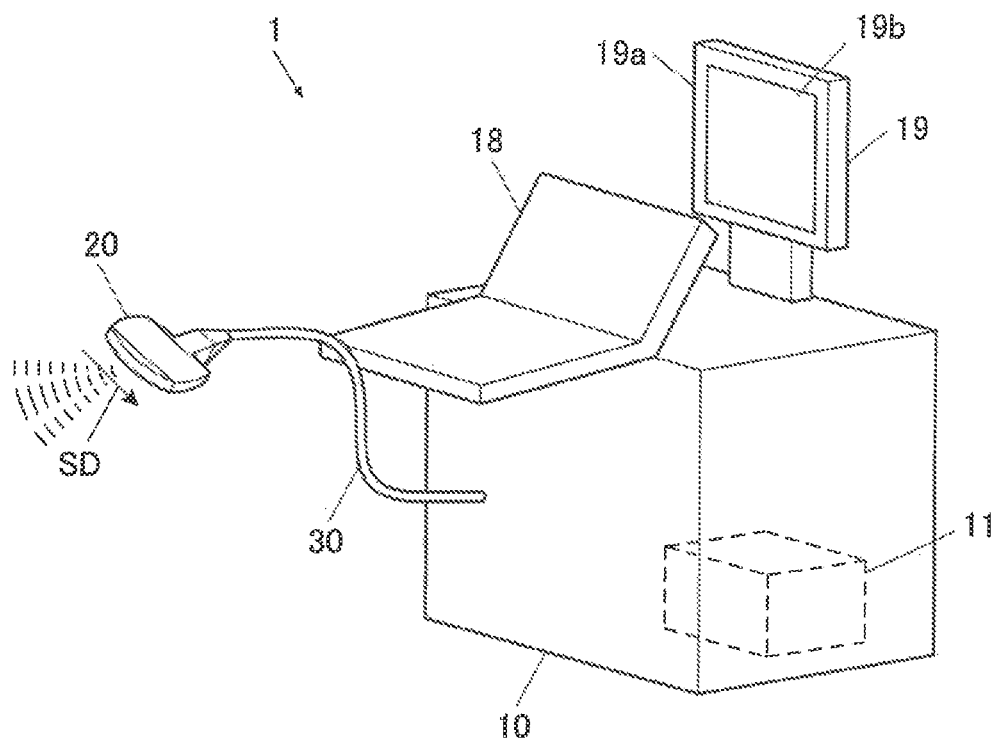
FIG. 1 shows a schematic configuration of an ultrasound diagnosis apparatus.

FIG. 1 shows a schematic configuration of an ultrasound diagnosis apparatus 1, which is a first embodiment of the present invention.

Figure 2:
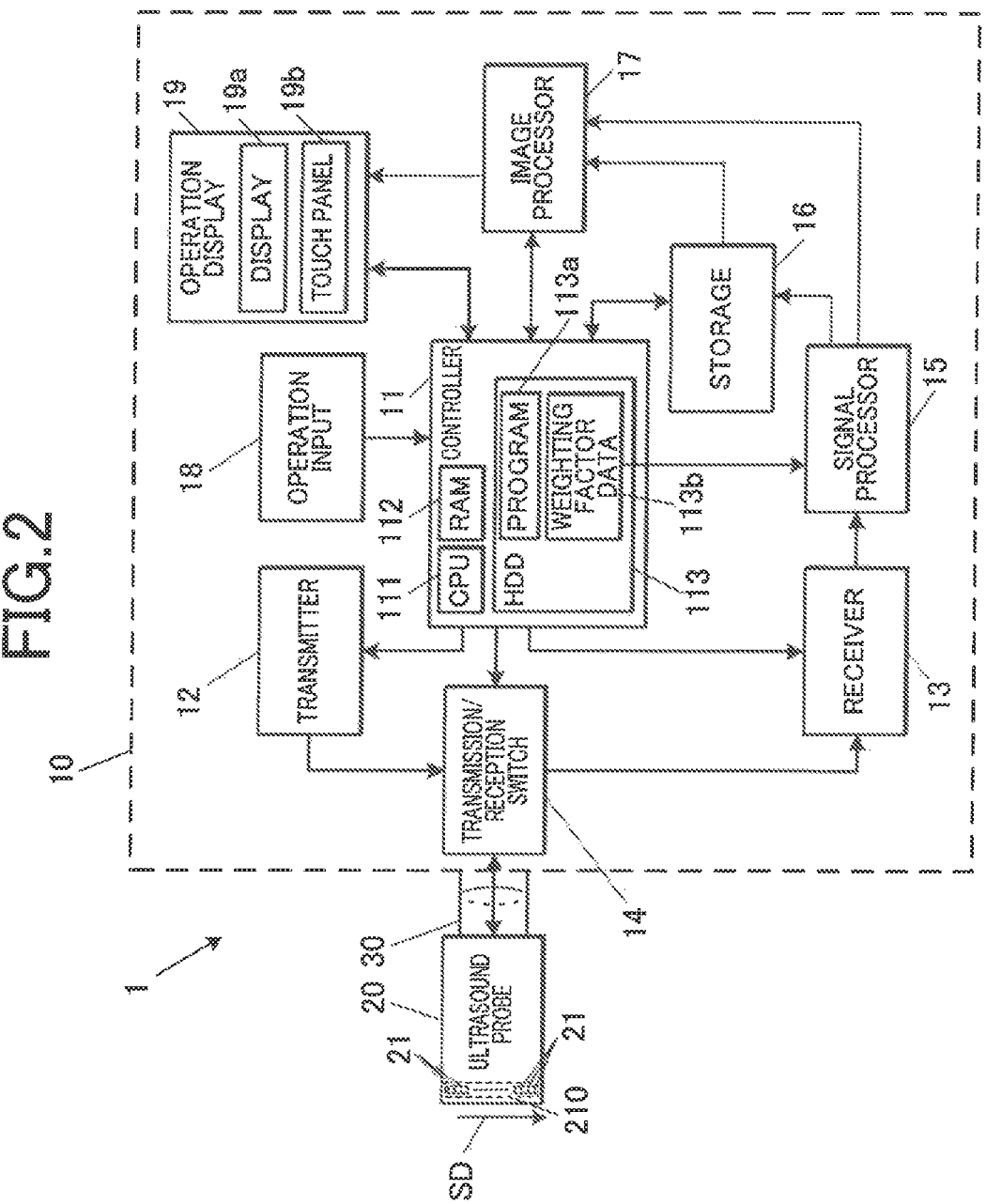
FIG. 2 is a block diagram showing main functional components of the ultrasound diagnosis apparatus.

FIG. 2 is a block diagram showing main functional components of the ultrasound diagnosis apparatus 1.

As shown in FIG. 1, the ultrasound diagnosis apparatus 1 includes an ultrasound diagnosis apparatus main body 10 and an ultrasound probe 20 connected to the ultrasound diagnosis apparatus main body 10 through a cable 30. The ultrasound diagnosis apparatus main body 10 includes a hardware processor 100 (computer), an operation input 18 including an operation table, an operation display 19 including a display 19a and a touch panel 19b, and the like. Among them, the operation input 18 and the touch panel 19b are included in an "input receiver".

The ultrasound diagnosis apparatus 1, under control of the hardware processor 100, outputs a drive signal to the ultrasound probe 20 to cause the ultrasound probe 20 to output ultrasound waves, based on an input operation carried out by an operator on an input device, such as a push button, a rotation input key, a slide switch, a toggle switch, a track ball, a keyboard, or a mouse, provided to the operation input 18, or based on a touch operation carried out by an operator on the touch panel 19b of the operation display 19. The ultrasound diagnosis apparatus 1 also acquires a received signal resulting from reception of ultrasound waves from the ultrasound probe 20, performs various types of processing, and causes the display 19a to display an ultrasound image or the like based on the received signal.

As shown in FIG. 2, the ultrasound diagnosis apparatus main body 10 includes a controller 11, a transmitter 12, a receiver 13, a transmission/reception switch 14, a signal processor 15, a storage 16, an image processor 17, the operation input 18, the operation display 19, and the like. Among them, the controller 11, the signal processor 15, and the image processor 17 are included in the "hardware processor which performs control", and the controller 11 is included in the "hardware processor which changes the setting". Moreover, the controller 11, the transmitter 12, the receiver 13, the transmission/reception switch 14, the signal processor 15, the storage 16, and the image processor 17 are included in the hardware processor 100.

The controller 11 includes a CPU 111 (Central Processing Unit), a RAM 112 (Random Access Memory), an HDD 113 (Hard Disk Drive) (non-transitory computer readable storage medium), and the like.

The CPU 111 reads a program 113a stored in the HDD 113, develops the program 113a in the RAM 112, and performs overall control of operations of each component of the ultrasound diagnosis apparatus 1 in accordance with the developed program 113a.

The RAM 112, which is a volatile memory such as an SRAM or a DRAM, provides a work space on the memory for the CPU 111 and stores transitory data.

The HDD 113 stores various types of setting data and image files generated by the ultrasound diagnosis apparatus 1, in addition to the above-mentioned program 113a. The setting data includes information on setting of attenuation correction, which will be described later, and weighting factor data 113b used to change the setting of attenuation correction. Note that any of other various publicly known data-writable storage devices, such as an SSD (Solid State Drive), may be used in place of the HDD 113 (or in addition to the HDD 113).

The transmitter 12 outputs a pulse signal (drive signal) to be supplied to the ultrasound probe 20 in accordance with a control signal input from the controller 11, and causes the ultrasound probe 20 to generate ultrasound waves. The transmitter 12 includes, for example, a clock generation circuit, a pulse generation circuit, a pulse width setter, and a delay circuit. The clock generation circuit is a circuit which generates a clock signal that determines a transmission timing and a transmission frequency of the pulse signal. The pulse generation circuit is a circuit which generates a bipolar rectangular-wave pulse with a preset voltage amplitude at a predetermined cycle. The pulse width setter sets a pulse width of the rectangular-wave pulse output from the pulse generation circuit. Each rectangular-wave pulse generated by the pulse generation circuit is branched into different interconnection paths for individual oscillators 21 of the ultrasound probe 20 before or after the rectangular-wave pulse is input to the pulse width setter. The delay circuit is a circuit which delays outputting the generated rectangular-wave pulse by a delay time period, which is set for each of the interconnection paths, according to a timing of transmitting to each oscillator 21.

The receiver 13, in accordance with control by the controller 11, acquires a received signal input from the ultrasound probe 20 and generates sound ray data (acoustic ray data) based on the received signal. Here, the sound ray data is data that is generated based on the received signal of a series of reflected waves generated as a result of a one-time transmission of ultrasound waves. Accordingly, the sound ray data includes information on reflection intensity (the strength of the received signal) at each location in a depth direction of a subject.

The receiver 13 includes, for example, an amplifier, an A/D conversion circuit, and a phasing addition circuit. The amplifier is a circuit which amplifies the received signal corresponding to the ultrasound waves received by each oscillator 21 of the ultrasound probe 20 at a predetermined amplification factor, which is preset. The A/D conversion circuit is a circuit which converts the amplified received signal into digital data at a predetermined sampling frequency. The phasing addition circuit is a circuit which adjusts the time phase of the A/D converted received signal by giving a delay time for each interconnection path corresponding to each oscillator 21, respectively, and generates the sound ray data by adding the adjusted time phases (phasing addition).

The transmission/reception switch 14, based on control by the controller 11, performs switching operation to cause the transmitter 12 to transmit a drive signal to the oscillators 21 when causing the oscillators 21 to oscillate ultrasound waves, and to output the received signal to the receiver 13 when acquiring a signal related to the ultrasound waves emitted by the oscillators 21.

The signal processor 15 performs various types of data processing on the sound ray data of the ultrasound waves, for purposes of compressing a data amount, adjusting the image quality of an ultrasound image, and the like. For example, when an ultrasound image is displayed in B mode or M mode, in which the strength of a received signal is represented by brightness, the signal processor 15 performs envelope detection processing, log compression processing, and the like on the sound ray data, and converts the sound ray data into data representing brightness values by performing gain adjustment, dynamic range adjustment, and the like. The sound ray data subjected to such processing (hereinafter, also referred to as the processed sound ray data) is output to the storage 16 and the image processor 17.

The storage 16 includes, for example, a volatile memory such as a DRAM (Dynamic Random Access Memory). Alternatively, any of various high-speed rewritable non-volatile memories may be used in place of the volatile memory (or in addition to the volatile memory).

The storage 16 stores the processed sound ray data output from the signal processor 15 in units of frames of an ultrasound image. The processed sound ray data stored in the storage 16 is data for reproduction that is used in control for reproducing and displaying part of ultrasound images displayed as a live moving picture, as a reproduced image. The data for reproduction stored in the storage 16 is read and output to the image processor 17 when necessary in accordance with control by the controller 11.

Note that the storage 16 may be included in hardware shared with the RAM 112. That is, the RAM 112 may have the function of the storage 16. Moreover, part of the above-mentioned data stored in the storage 16 may be stored in the HDD 113.

The image processor 17 generates image data in a format according to a display method of the display 19a by performing predetermined image processing on the processed sound ray data output from the signal processor 15 or the storage 16.

The image processor 17 includes a DSC (Digital Signal Converter), an image synthesizer, and the like.

The DSC performs coordinate transformation, pixel interpolation, frame rate adjustment, and the like on frame data of the processed sound ray data, thereby converting the frame data conforming to a coordinate system of the received signal into frame data (image data) conforming to a display coordinate system of the display 19a.

The image synthesizer combines image data of an operation button, a body mark, and a scale to be displayed on an ultrasound diagnosis screen including an ultrasound image, with the image data of the ultrasound image, thereby generating the synthesized image data.

Part or all of the functions of the controller 11, the transmitter 12, the receiver 13, the transmission/reception switch 14, the signal processor 15, the storage 16, and the image processor 17 included in the hardware processor 100 as described above can be implemented by using hardware circuits (integrated circuits) such as an ASIC (Application Specific Integrated Circuit), an FPGA (Field Programmable Gate Array), and a DSP (Digital Signal Processor). Two or more of the functions of these components may be incorporated into a shared integrated circuit.

The operation input 18 includes physical operation parts such as a push button, a rotation input key, a slide switch, a toggle switch, a track ball, a keyboard, and a mouse, and converts an input operation carried out by an operator on any of the physical operation parts into an operation signal and outputs the operation signal to the controller 11.

The display 19a of the operation display 19 includes a display screen using any one of various display methods such as an LCD (Liquid Crystal Display), an organic EL (Electro-Luminescence) display, an inorganic EL display, a plasma display, and a CRT (Cathode Ray Tube) display, and a driver of the display screen. The display 19a generates a drive signal for the display screen (each display pixel) according to a control signal output from the controller 11 or image data generated by the image processor 17, and displays on the display screen a menu and a status related to ultrasound diagnosis, an operation button representing an object of a touch operation that is received through the touch panel 19b, and measurement data such as an ultrasound image based on received ultrasound waves.

The touch panel 19b of the operation display 19 is a capacitive touch panel overlaid on the display screen of the display 19a. The touch panel 19b senses a touch (touch operation) based on a change in capacitance between an internal conductive layer and a surface that is caused by the surface being touched by a fingertip or the like of an operator, and outputs a signal indicating a location (coordinates) where the touch is sensed, as an operation signal, to the controller 11. Note that the method used for the touch panel 19b is not limited to capacitive sensing, and any of other methods such as resistive touch and electromagnetic induction touch may also be used.

The operation input 18 and the operation display 19 may be provided on a housing of the ultrasound diagnosis apparatus main body 10 in an integrated manner, or may be provided externally and attached to the ultrasound diagnosis apparatus main body 10 through a cable or the like. If an operation input terminal and a display output terminal are provided to the ultrasound diagnosis apparatus main body 10, conventional peripheral equipment for operation and for display may be connected to such terminals and used.

In FIG. 1, the operation input 18 and the operation display 19 are provided separately. However, the operation input 18 and the operation display 19 may be configured as a single unit. For example, the various operation button, track ball, and the like of the operation input 18 may be provided on a housing of the operation display 19 including the display 19a and the touch panel 19b.

The ultrasound probe 20 oscillates ultrasound waves (here, at approximately 1 to 30 MHz) and transmits (emits) the ultrasound waves to a subject such as a living body, and also functions as an acoustic sensor which receives reflected waves (echoes) that are reflected ones of the transmitted ultrasound waves inside the subject. The ultrasound probe 20 includes an oscillator array 210 that is an array of the plurality of oscillators 21 which transmit and receive the ultrasound waves.

The oscillator array 210 is an array of the plurality of oscillators 21, each of which includes a piezoelectric device. The piezoelectric device includes a piezoelectric material and electrodes provided at both ends of the piezoelectric material, and electric charge occurs at the electrodes due to deformation (expansion and contraction) of the piezoelectric material. By supplying a voltage pulse (pulse signal) to the oscillators 21, each piezoelectric material deforms depending on an electric field occurring in each piezoelectric material, whereby ultrasound waves are oscillated. When ultrasound waves of a predetermined frequency band enter the oscillators 21, a caused sound pressure changes (oscillates) the thickness of each piezoelectric material, whereby electric charge according to the changed amount occurs at both ends of the piezoelectric material in a thickness direction thereof, and electric charge in an amount according to the occurring electric charge is induced at the electrodes at both ends of the piezoelectric device. For the piezoelectric material, a ferroelectric material is used here.

In the ultrasound probe 20 in the present embodiment, the oscillator array 210 includes 192 oscillators 21 that are one-dimensionally arrayed in a predetermined oscillator array direction. Alternatively, the oscillators 21 may be two-dimensionally arrayed in such a manner that some are arrayed also in a direction orthogonal to the oscillator array direction. The number of the oscillators 21 can be set arbitrarily. The ultrasound probe 20 in the present embodiment transmits ultrasound waves from a set of consecutive oscillators 21 (for example, 64 oscillators 21) of the 192 oscillators 21 based on a pulse signal from the transmitter 12. Each time ultrasound waves are generated, a set of oscillators 21 to transmit ultrasound waves is shifted by a predetermined number of oscillators 21 in the oscillator array direction, whereby scanning is performed in a scanning direction SD parallel to the oscillator array direction. Moreover, the ultrasound probe 20 used in the present embodiment is of a convex electronic scanning type, in which the range in a transmission direction of the ultrasound waves transmitted at different timings forms a fan-like shape. Note that for the ultrasound probe 20, any of various electronic scanning methods, such as linear electronic scanning and sector electronic scanning, and various mechanical scanning methods, such as linear scanning, sector scanning, arc scanning, and radial scanning, may be adopted. The bandwidth of a received frequency of ultrasound waves at the ultrasound probe 20 can be set arbitrarily.

The ultrasound diagnosis apparatus 1 can be configured such that any of a plurality of different ultrasound probes 20 can be connected to the ultrasound diagnosis apparatus main body 10 and used, depending on a subject of diagnosis.

The cable 30 includes, at one end thereof, a connector (not shown) to connect to the ultrasound diagnosis apparatus main body 10. The ultrasound probe 20 is configured to be attachable to and detachable from the ultrasound diagnosis apparatus main body 10 through the cable 30.

Next, a description will be given of various operations related to setting of attenuation correction performed by the ultrasound diagnosis apparatus 1 of the present embodiment.

As described above, ultrasound waves transmitted from the ultrasound probe attenuate as the ultrasound waves go deeper into a subject. The strength of a received signal obtained by receiving reflected waves of the ultrasound waves becomes lower as the depth of a location where the ultrasound waves are reflected (reflection depth) inside the subject becomes greater (deeper). Therefore, from an ultrasound image in B mode, in which the strength of a received signal is converted into brightness for display, it is difficult to make an accurate diagnosis due to lowered visibility because the brightness is lower at portions where reflection depth inside a subject is greater.

Accordingly, the ultrasound diagnosis apparatus 1 of the present embodiment displays an ultrasound image after performing attenuation correction (TGC or STC) that corrects the strength of a received signal lowered due to attenuation of ultrasound waves by making the gain (correction amount) of a received signal larger as the reflection depth of ultrasound waves is greater (that is, time passing from transmission until reception is longer), so as to uniform brightness in the ultrasound image.

Specifically, in the ultrasound diagnosis apparatus 1, as setting of attenuation correction, a gain of a received signal is set for each of a plurality of depth segments D (for example, depth segments D1 to D8 in FIG. 3), which are obtained by segmenting an ultrasound image in the depth direction. When an ultrasound image is displayed, the signal processor 15 performs processing for amplifying each part of sound ray data by using the gains based on the above-mentioned setting of attenuation correction. That is, the signal processor 15 generates processed sound ray data by amplifying each part of sound ray data output from the receiver 13 by using one of the gains corresponding to a reflection depth of the ultrasound waves corresponding to the part (that is, by correcting each part with a correction amount according to a reflection depth). The processed sound ray data is converted into image data by the image processor 17, and an ultrasound image is displayed, whereby the ultrasound image subjected to appropriate attenuation correction can be displayed.

In the ultrasound diagnosis apparatus 1 of the present embodiment, the setting of attenuation correction can be changed by a user. Hereinafter, operations related to such changing of the setting of attenuation correction will be described.

Figure 3:
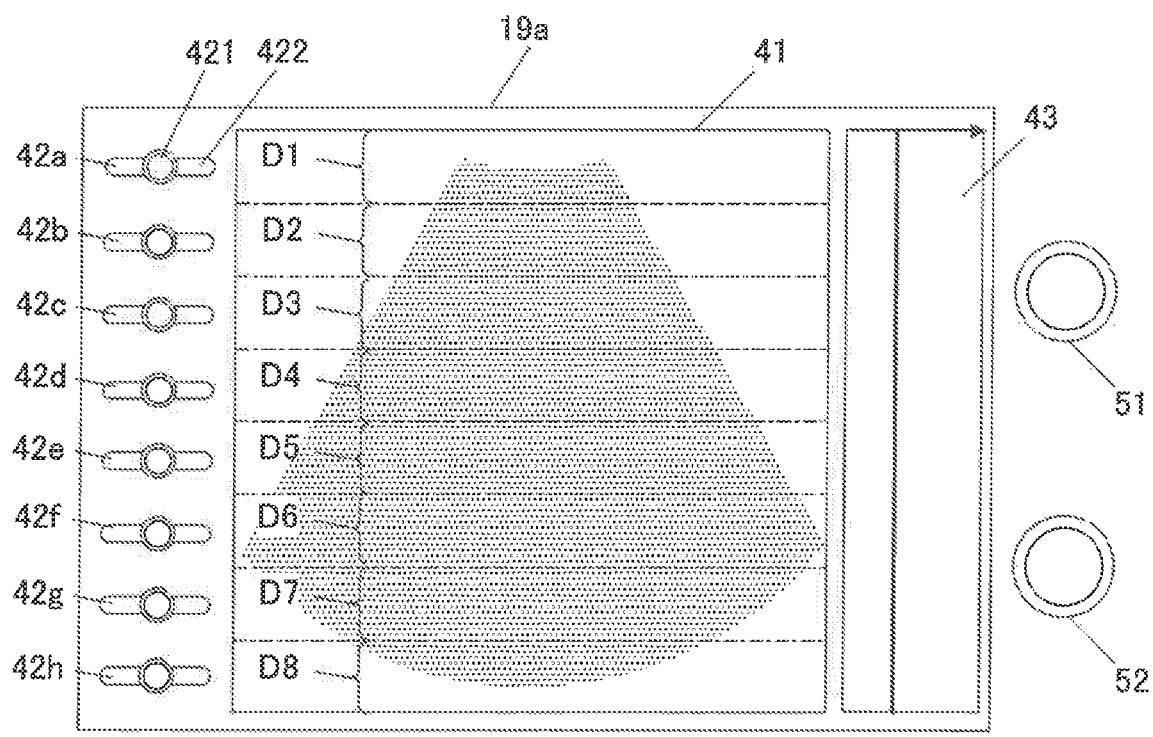
FIG. 3 shows an example of an attenuation correction setting screen and an input receiver used for setting.

FIG. 3 shows an example of an attenuation correction setting screen and an input receiver used for setting. FIG. 3 depicts an attenuation correction setting screen, which is displayed on the display 19a, and a first rotation input key 51 (first input operation receiver) and a second rotation input key 52 (second input operation receiver) of the operation input 18, which are used for setting of attenuation correction. The setting screen is displayed when a predetermined input operation that requests a change in the setting of attenuation correction is carried out by a user on the operation input 18 or the touch panel 19b.

In the setting screen shown in FIG. 3, an ultrasound image 41, slider bars 42a to 42h (correction amount images) (hereinafter, also referred to as the slider bars 42 if no distinction is made from each other), and a gain distribution image 43.

The ultrasound image 41 may be a live moving picture, in which ultrasound images are sequentially updated based on new received signals while scanning with ultrasound waves is performed, or may be a still image obtained by freezing (stopping) a live moving picture. In the following description, eight segments obtained by dividing the ultrasound image 41 into eight equal parts in the depth direction will be referred to as the depth segments D1 to D8 in order starting from a shallowest one.

The slider bars 42a to 42h are displayed at locations corresponding to the depth segments D1 to D8, respectively. On each slider bar 42, a knob 421 is moved rightward or leftward along a rail 422 in a state where a user keeps a touch operation with a finger or the like on the knob 421, and the touch operation is stopped at a desired location, whereby an adjustment amount corresponding to the location of the moved knob 421 can be input. Here, when an operation is carried out on any one of the slider bars 42, a gain in a depth segment D corresponding to the operated slider bar 42 is changed according to the operation. That is, it is possible to individually adjust a gain in a specified depth segment D through a slider bar 42.

The gain in each depth segment D set by using each slider bar 42 is a gain at a representative reflection depth in the depth segment D, which can be, for example, a gain at a middle of the depth segment D in the depth direction. A gain at each reflection depth other than the representative reflection depth in each depth segment D can be set by calculation through linear interpolation or curve approximation.

In the gain distribution image 43, a gain distribution graph is displayed, with a vertical axis representing reflection depth and a horizontal axis representing the gain of a received signal. In FIG. 3, since gains in the depth segments D1 to D8 are not adjusted, a graph with uniform gains at all the reflection depths is shown.

The ultrasound diagnosis apparatus 1 of the present embodiment is configured such that, in addition to individual detailed gain adjustment in each depth segments D performed by using the slider bars 42, rough gain adjustment across two or more of the depth segments D can be performed by using the first rotation input key 51 and the second rotation input key 52.

Figure 4A:
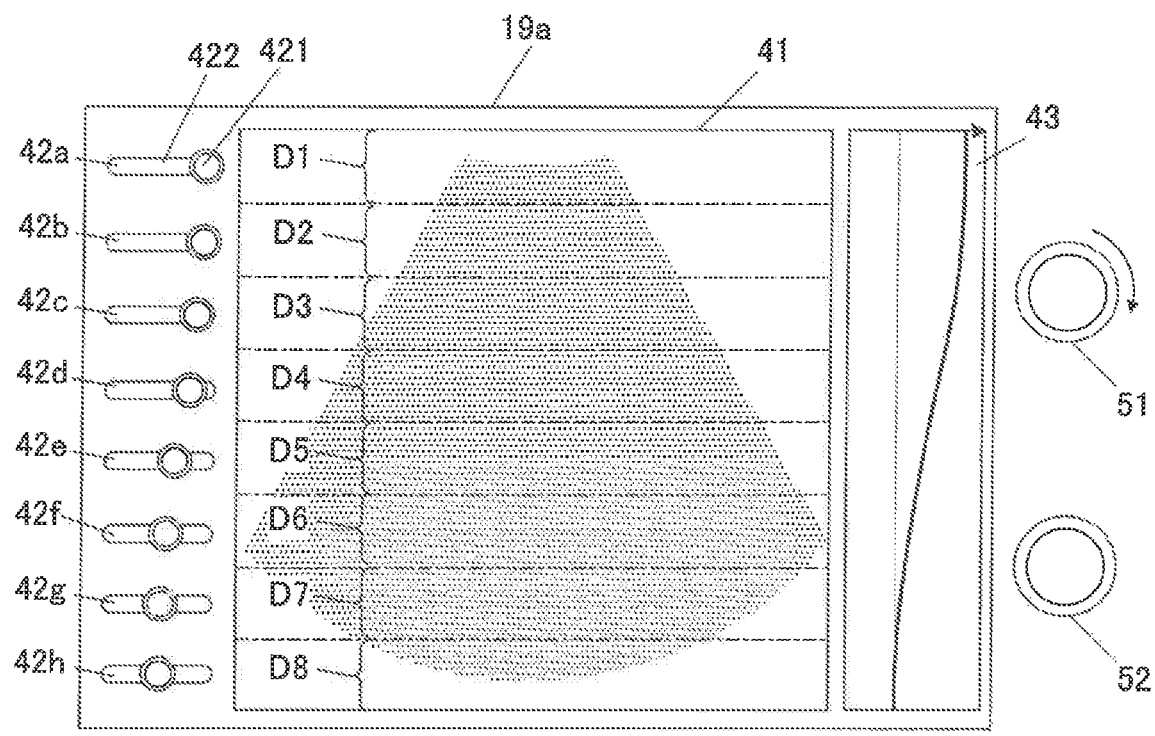
FIG. 4A shows a state of setting of attenuation correction when a first rotation input key is rotated.

FIG. 4A shows a state of setting of attenuation correction when the first rotation input key 51 is rotated from the state shown in FIG. 3.

As shown in FIG. 4A, the knobs 421 of the slider bars 42a to 42g move rightward in conjunction with a clockwise rotation of the first rotation input key 51, whereby settings of gains at reflection depths corresponding to the multiple adjacent depth segments D1 to D7 are changed at a time. In accordance with the changes in the gains, the gain distribution graph in the gain distribution image 43 is updated. If a live moving picture is displayed in the ultrasound image 41, a live moving picture is displayed using ultrasound images subjected to attenuation correction based on the changed gains.

Here, the amounts of the changes in the gains in the depth segments D1 to D7 (the amounts of the movements of the knobs 421 of the slider bars 42a to 42g) according to the rotation of the first rotation input key 51 have a largest amount in the shallowest depth segment D1 (first depth segment), gradually decrease as the depth becomes greater, and have a smallest amount in the depth segment D7. Note that a gain in the depth segment D8 is not changed by a rotation of the first rotation input key 51.

Figure 4B:
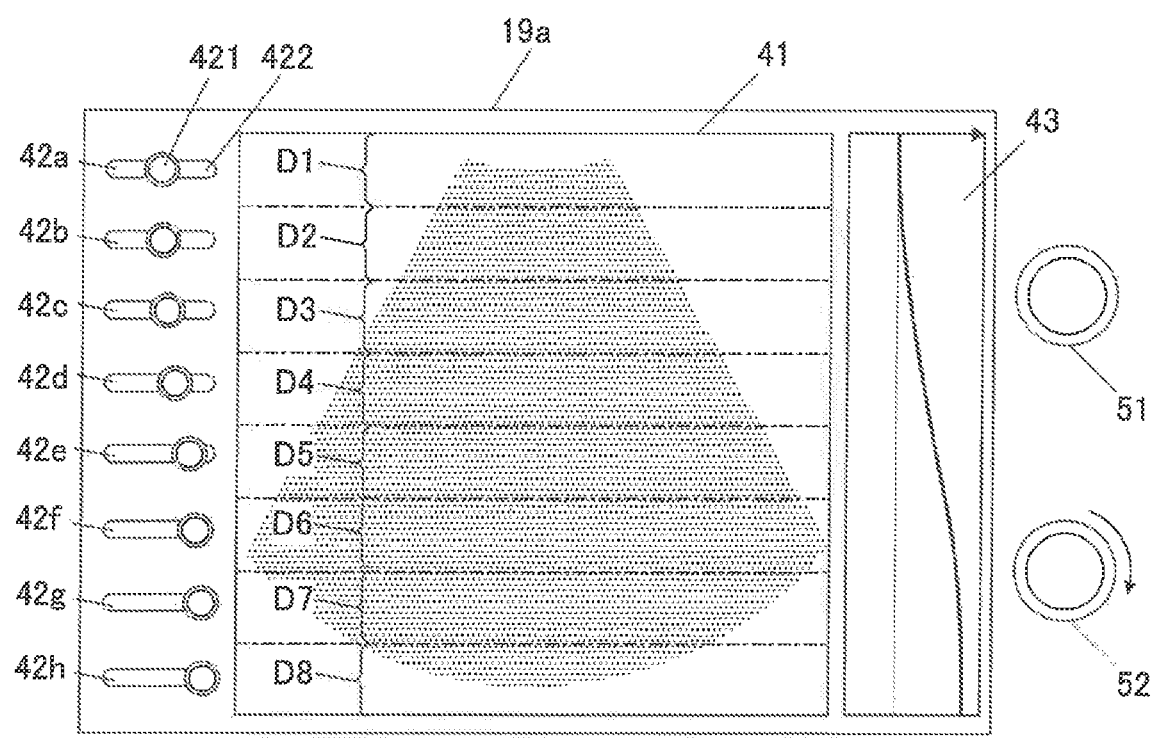
FIG. 4B shows a state of setting of attenuation correction when a second rotation input key is rotated.

FIG. 4B shows a state of setting of attenuation correction when the second rotation input key 52 is rotated from the state shown in FIG. 3.

As shown in FIG. 4B, the knobs 421 of the slider bars 42b to 42h move rightward in conjunction with a clockwise rotation of the second rotation input key 52, whereby settings of gains at reflection depths corresponding to the multiple adjacent depth segments D2 to D8 are changed at a time. In accordance with the changes in the gains, the gain distribution graph in the gain distribution image 43 is updated.

Here, the amounts of the changes in the gains in the depth segments D2 to D8 (the amounts of the movements of the knobs 421 of the slider bars 42b to 42h) according to the rotation of the second rotation input key 52 have a largest amount in the deepest depth segment D8 (second depth segment), gradually decrease as the depth becomes less, and have a smallest amount in the depth segment D2. A gain in the depth segment D1 is not changed by a rotation of the second rotation input key 52.

Processing for changing gains with weights according to reflection depths as described above is performed as follows. That is, when an input operation of rotating the first rotation input key 51 or the second rotation input key 52 is carried out, an adjustment amount for setting of attenuation correction is input (designated) depending on the amount of the rotation. When the adjustment amount is designated, a gain in each of the multiple depth segments D is individually set to an amount according to a product of the designated adjustment amount and a weighting factor corresponding to a reflection depth corresponding to the depth segment D. The content of each slider bar 42 is changed to a content indicating the corresponding correction amount set according to the above-mentioned input operation.

FIG. 5 shows an example of the contents of the weighting factor data 113b, which is used to change gains through the first rotation input key 51 and the second rotation input key 52.

In the weighting factor data 113b, a combination of weighting factors (weighting factor information In) corresponding to the depth segments D1 to D8, respectively, is set for each of the first rotation input key 51 and the second rotation input key 52. Of the weighting factor data 113b in FIG. 5, data related to the weighting factors associated with the first rotation input key 51 is included in first weighting factor information, and data related to the weighting factors associated with the second rotation input key 52 is included in second weighting factor information.

When an input operation of rotating the first rotation input key 51 or the second rotation input key 52 is carried out, an adjustment amount designated by the amount of the rotation is multiplied by the above-mentioned weighting factors, whereby a changed gain in each depth segment D is calculated and set. The respective displayed contents of the slider bars 42a to 42h are changed based on values of the calculated gains, and the gain distribution graph in the gain distribution image 43 is updated.

Note that the amount of a change in each gain may be a resultant of multiplying a product of the adjustment amount based on the rotation input and a corresponding weighting factor by a predetermined constant. That is, the weighting factors may be values proportional to the amounts of changes in gains.

In the foregoing, an example is described in a case where the first rotation input key 51 and the second rotation input key 52 are rotated clockwise. However, when the first rotation input key 51 and the second rotation input key 52 are rotated counterclockwise, the knobs 421 of the slider bars 42a to 42h move leftward by respective amounts corresponding to the above-mentioned weighting factors corresponding to the reflection depths, and in response, a gain in each depth segment D is changed to decrease.

As described above, gains mainly in depth segments D with smaller reflection depths can be changed at a time by using the first rotation input key 51, and gains mainly in depth segments D with greater reflection depths can be changed at a time by using the second rotation input key 52. Moreover, gain adjustment using the first rotation input key 51 and gain adjustment using the second rotation input key 52 can be combined. After gain adjustment is performed by using the first rotation input key 51 and the second rotation input key 52, individual gain adjustment can also be performed for each depth segment D by using the slider bars 42a to 42h.

A plurality of sets of the weighting factor information In associated with the first rotation input key 51 and a plurality of sets of the weighting factor information In associated with the second rotation input key 52 may be prepared correspondingly to various types of diagnosis settings of the ultrasound diagnosis apparatus 1, and weighting factor information In corresponding to a current diagnosis setting may be selected and used for setting of attenuation correction.

For example, as shown in FIG. 6, a plurality of sets of weighting factor information In may be prepared beforehand correspondingly to depth settings of an ultrasound image (that is, settings of the range, in the depth direction, of parts of a subject to be displayed as an ultrasound image, which are shown as depth settings A, B, and C in FIG. 6), and setting of attenuation correction may be changed based on weighting factor information In corresponding to the depth setting of a ultrasound image to be displayed.

In the depth settings shown in FIG. 6, it is assumed that a greatest reflection depth included in an ultrasound image in the depth setting B is greater than that of the depth setting A, and that a greatest reflection depth included in an ultrasound image in the depth setting C is greater than that of the depth setting B. In this case, the number of depth segments D in which gains are adjusted according to a rotation of the first rotation input key 51 is reduced in the order of the depth settings A, B, C as shown in FIG. 6, whereby when depth settings are changed, gain settings in a same diagnosis area of a subject can avoid greatly varying. For example, in a case where an affected part displayed in the depth segment D7 in the depth setting A is displayed in the depth segment D6 in the depth setting B and is displayed in the depth segment D5 in the depth setting C, a weighting factor corresponding to the depth segment D7 in the depth setting A, a weighting factor corresponding to the depth segment D6 in the depth setting B, and a weighting factor corresponding to the depth segment D5 in the depth setting C are uniformly set to "1" as shown in FIG. 6, whereby even if depth settings are changed, the sensitivity of gain adjustment at the location of the affected part according to a rotation operation on the first rotation input key 51 can be made constant. Thus, a gain at a diagnosis site can be adjusted to a desired state through an intuitional input operation.

Similarly, a plurality of sets of weighting factor information In may be generated beforehand correspondingly to a plurality of ultrasound probes 20 of different types, and setting of attenuation correction may be changed based on weighting factor information In corresponding to the type of an ultrasound probe 20 currently used.

A plurality of sets of weighting factor information In may also be generated beforehand correspondingly to a plurality of different diagnosis sites (finger, elbow, shoulder, knee, ankle, toe, head, neck, abdomen, mammary gland, thyroid gland, heart, fetus, and the like) of a subject, and setting of attenuation correction may be changed based on weighting factor information In corresponding to a diagnosis site to be diagnosed.

Next, a description will be given of a control procedure performed by the controller 11, of processing related to setting of attenuation correction.

FIG. 7 is a flowchart showing a control procedure of attenuation correction setting processing.

When the attenuation correction setting processing is started, the hardware processor 100 acquires weighting factor information In corresponding to a current diagnosis setting of the ultrasound diagnosis apparatus 1 from the weighting factor data 113b (step S101).

Subsequently, the hardware processor 100 determines whether or not an input operation of rotating the first rotation input key 51 or the second rotation input key 52 is carried out (step S102). When determining that such an input operation is carried out ("YES" in step S102), the hardware processor 100 calculates a corrected gain for each of the depth segments D1 to D8 by multiplying an adjustment amount designated by the input operation by the weighting factors acquired in step S101 (step S103). The hardware processor 100 updates setting of attenuation correction based on the values of the corrected gains and stores the setting of attenuation correction in the HDD 113.

When the processing in step S103 is completed, or when it is determined in step S102 that an input operation of rotating the first rotation input key 51 or the second rotation input key 52 is not carried out ("NO" in step S102), the hardware processor 100 determines whether or not a touch operation on any of the slider bars 42 is carried out (step S104). When such a touch operation is carried out ("YES" in step S104), the hardware processor 100 changes a gain setting in a corresponding depth segment D according to the indication of the touch operation (step S105).

When the processing in step S105 is completed, or when it is determined in step S104 that a touch operation on any of the slider bars 42 is not carried out ("NO" in step S104), the hardware processor 100 determines whether or not a predetermined operation to complete setting of attenuation correction is carried out (step S106). When determining that such an operation is not carried out ("NO" in step S106), the hardware processor 100 moves processing to step S102. When determining that such an input operation is carried out ("YES" in step S106), the hardware processor 100 terminates the attenuation correction setting processing.

Next, various modifications of the above-described embodiment will be described. The modifications are related to variations of the input receiver used to input adjustment values in setting of attenuation correction, and the others are similar to those of the above-described embodiment. Hereinafter, differences from the above-described embodiment will be described.

Modification 1

Modification 1 is different from the above-described embodiment in that the functions of the first rotation input key 51 and the second rotation input key 52 are implemented with a single rotation input key 50.

FIG. 8 shows the rotation input key 50 according to the modification 1.

The amount of protrusion of the rotation input key 50 from an operation plane of the operation input 18 can be adjusted to two states. The rotation input key 50 is a push and rotate key on which a rotation operation can be carried out in each one of the states. That is, by pushing down a circular upper portion of the rotation input key 50 in a first state in FIG. 8, the rotation input key 50 can be shifted to a second state in which the amount of protrusion from the operation plane is relatively small. Moreover, by pushing down the upper portion of the rotation input key 50 in the second state, an internal lock defining the height of the rotation input key 50 in the second state is released, and the rotation input key 50 can be shifted to the first state.

The rotation input key 50 in the first state operates in a first input mode, and the rotation input key 50 in the second state operates in a second input mode. Here, the rotation input key 50 in the first input mode has the same function as the first rotation input key 51 in the above-described embodiment, and the rotation input key 50 in the second input mode has the same function as the second rotation input key 52 in the above-described embodiment. That is, by bringing the rotation input key 50 in the first state and carrying out a rotation operation thereon, gains mainly in depth segments D with smaller reflection depths can be changed at a time, and by bringing the rotation input key 50 in the second state and carrying out a rotation operation thereon, gains mainly in depth segments D with greater reflection depths can be changed at a time.

Note that in FIG. 8, a description is given by using an example in which the input modes of the rotation input key 50 are changed in two stages, the first state and the second state. However, the example is not intended as limitation. Input modes can be changed in three or more stages depending on a pushed amount. For example, a rotation input key 50 may be used, which can be changed to a third state (third input mode) in which the height of the rotation input key 50 is lower than in the second state, in addition to the first state (first input mode) and the second state (second input mode), and is configured to circulate among the three states in such a manner as to be changed to the first state, the second state, the third state, the first state, and so on each time the rotation input key 50 is pushed down.

In the rotation input key 50 of the present modification, an operation of pushing the rotation input key 50 to shift the rotation input key 50 between the first state and the second state corresponds to an input mode designation operation that designates an input mode, and an input operation of rotating the rotation input key 50 corresponds to an input operation that designates an adjustment amount for setting of attenuation correction.

Modification 2

Figure 9:
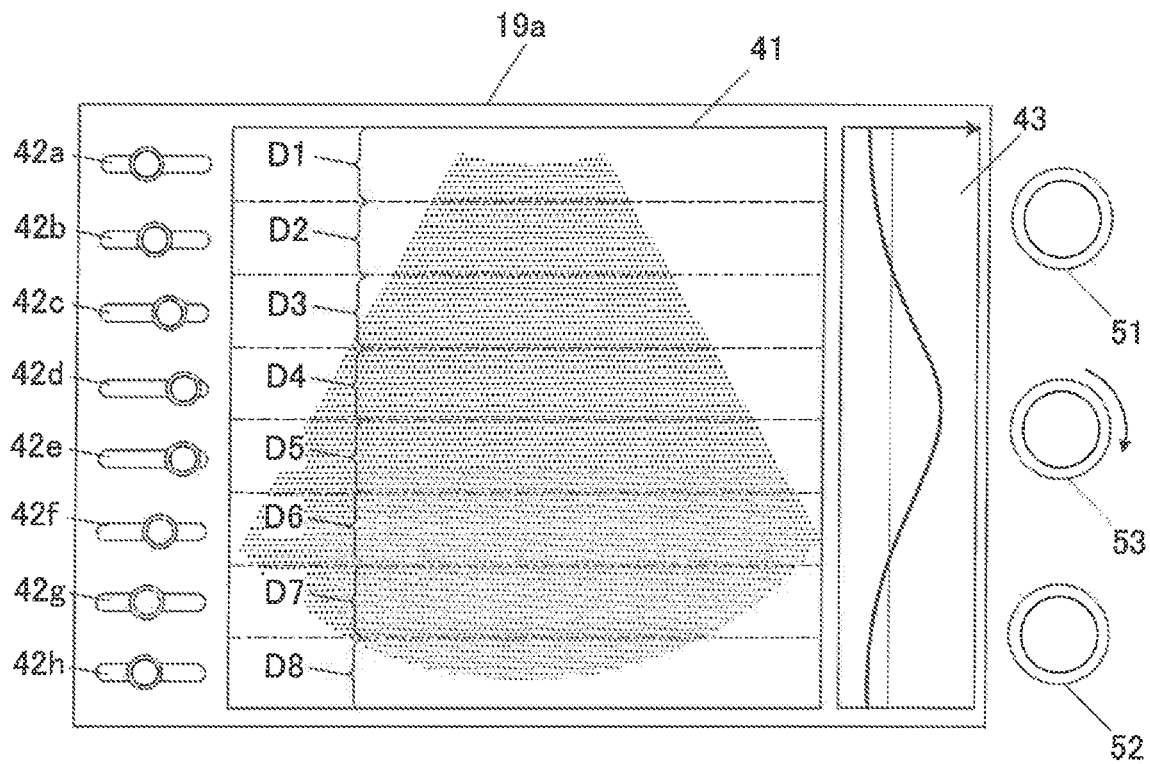
FIG. 9 shows an example of an attenuation correction setting screen and an input receiver used for setting according to modification 2.

FIG. 9 shows an example of an attenuation correction setting screen and an input receiver used for setting according to modification 2.

In the present modification, in addition to the first rotation input key 51 and the second rotation input key 52, a third rotation input key 53 (third input operation receiver) is provided to the operation input 18. FIG. 9 shows a state of setting of attenuation correction in a case where the third rotation input key 53 is rotated from a state where gains in all the depth segments D are unadjusted. In weighting factor information In (third weighting factor information) (not shown) associated with the third rotation input key 53, weighting factors are set such that weighting factors corresponding to the depth segments D4 and D5 (third depth segment) are largest, and the weighting factors decrease from the depth segment D4 toward the depth segment D1 and also decrease from the depth segment D5 toward the depth segment D8. Weighting factors corresponding to the depth segments D1, D2, D7, and D8 are negative values. Accordingly, as shown in the gain distribution image 43 in FIG. 9, when the third rotation input key 53 is rotated, gains in the depth segments D3 to D6 increase, while gains in the depth segments D1, D2, D7, and D8 decrease.

By combining the third rotation input key 53 as described above with the first rotation input key 51 and the second rotation input key 52, setting of attenuation correction can be adjusted more flexibly.

Modification 3

Figure 10:
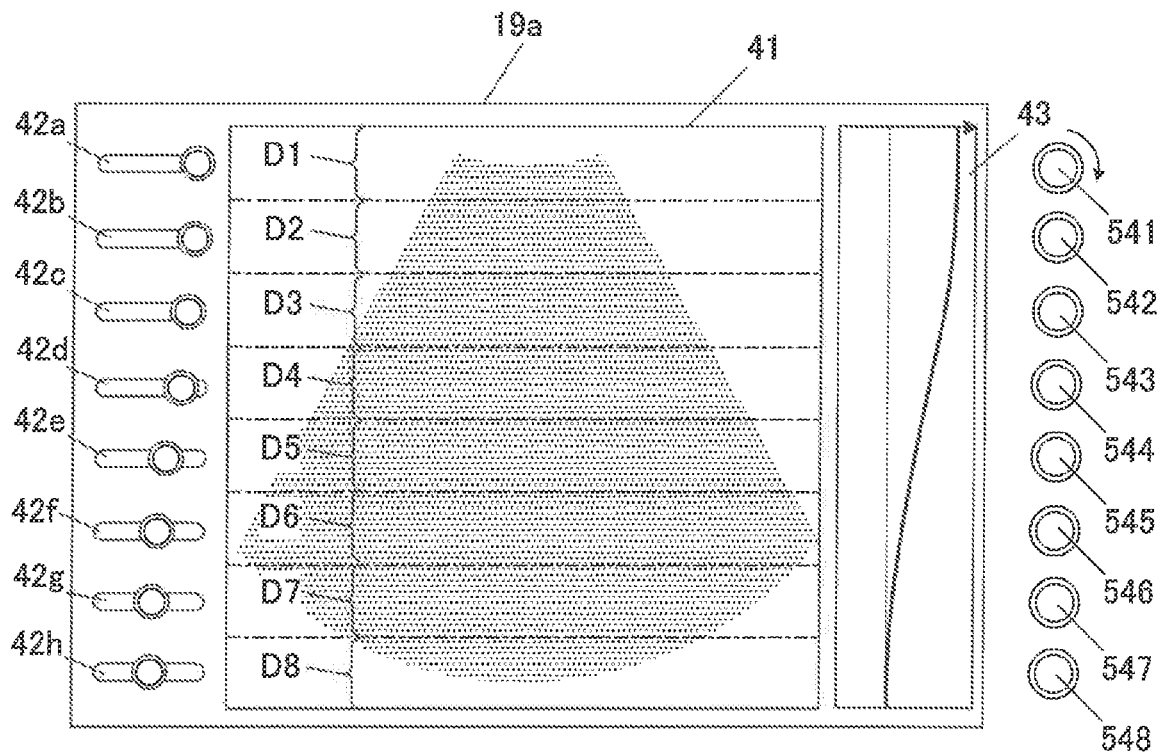
FIG. 10 shows an example of an attenuation correction setting screen and an input receiver used for setting according to modification 3.

FIG. 10 shows an example of an attenuation correction setting screen and an input receiver used for setting according to modification 3. As shown in FIG. 10, rotation input keys 541 to 548 (input operation receivers) corresponding to the depth segments D1 to D8, respectively, are provided to the operation input 18 in the present modification.

Figures 11, 12:
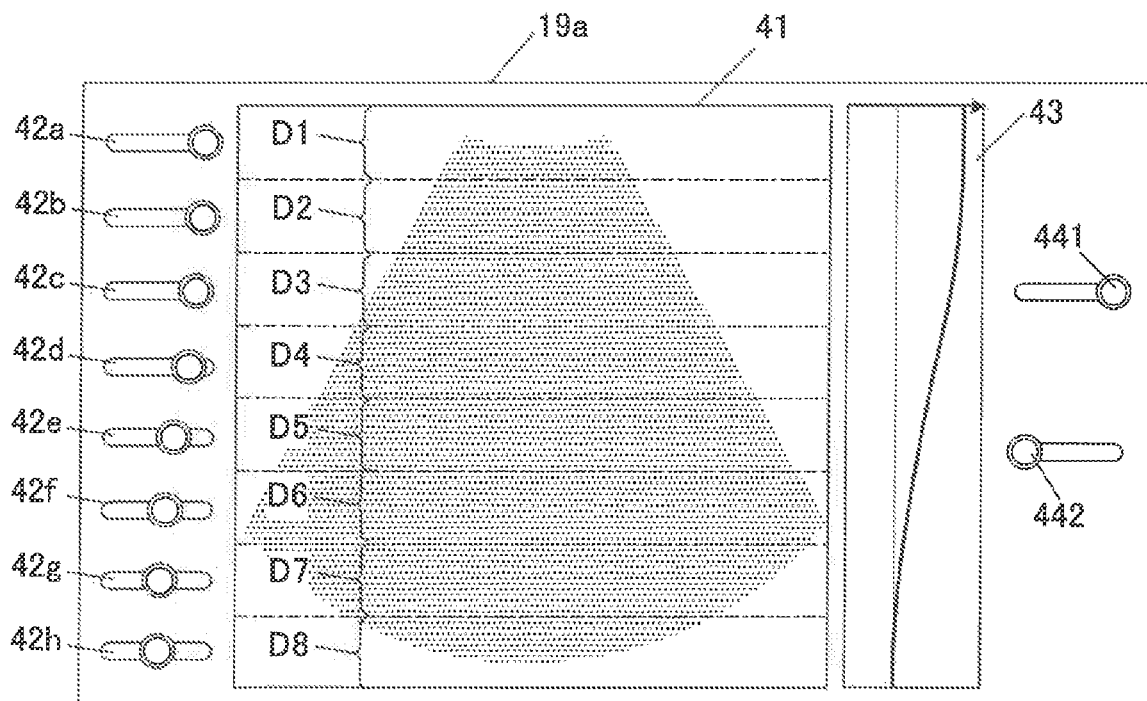
FIG. 11 shows an example of the contents of weighting factor data according to the modification 3.
FIG. 12 shows an example of an attenuation correction setting screen according to modification 4.

FIG. 11 shows an example of the contents of weighting factor data according to the modification 3. As shown in FIG. 11, in weighting factor information In associated with each of the rotation input keys 541 to 548, a largest weighting factor (10) is assigned to a depth segment D corresponding to the rotation input key. The rotation input keys 541 to 548 are provided in this manner, whereby while a gain in a target depth segment D is mainly adjusted, gains in multiple depth segments D adjacent to the target depth segment D can also be adjusted conjunctionally. Accordingly, desired setting of attenuation correction can be made more easily.

Modification 4

Figure 13:
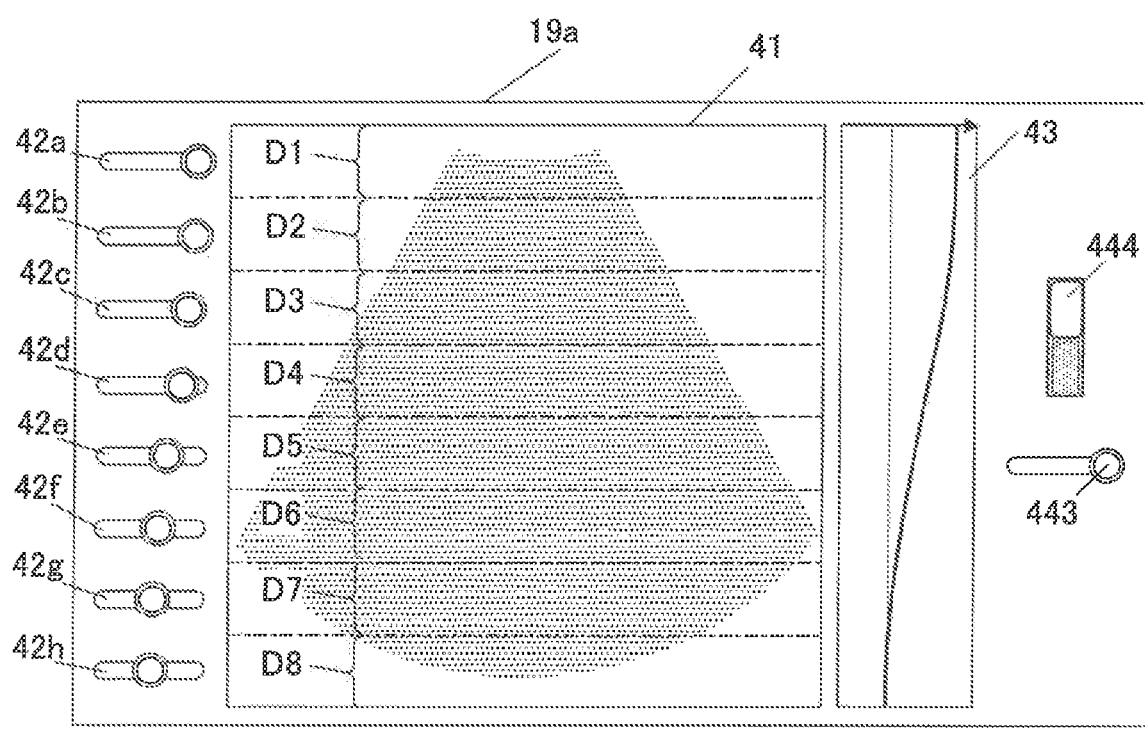
FIG. 13 shows another example of the attenuation correction setting screen according to the modification 4.

FIGS. 12 and 13 show examples of an attenuation correction setting screen according to modification 4. In the setting screen shown in FIG. 12, in addition to the contents of the setting screen shown in FIG. 3, a first slider bar 441 and a second slider bar 442 (operation object images) are displayed. By carrying out a touch operation on the first slider bar 441 of these slider bars, an adjustment value to change gains mainly in depth segments D with smaller reflection depths at a time can be input, similarly to the first rotation input key 51 in the above-described embodiment. By carrying out a touch operation on the second slider bar 442, an adjustment value to change gains mainly in depth segments D with greater reflection depths at a time can be input, similarly to the second rotation input key 52. Accordingly, in the example shown in FIG. 12, setting of attenuation correction as in above-described embodiment can be performed, without using the physical operation parts provided to the operation input 18.

In the setting screen shown in FIG. 13, in place of the first slider bar 441 and the second slider bar 442, a single slider bar 443 (operation object image) and a changing switch 444 for changing functions (input modes) of the slider bar 443 are displayed.

As shown in FIG. 13, the slider bar 443 operates with the same function as the first slider bar 441 in FIG. 12 (that is, the same function as the first rotation input key 51) in a state where the changing switch 444 is turned to a smaller-depth side (toward the top of the figure). On the other hand, the slider bar 443 operates with the same function as the second slider bar 442 in FIG. 12 (that is, the same function as the second rotation input key 52) in a state where the changing switch 444 is turned to a greater-depth side (toward the bottom of the figure). With the configuration of the operation buttons as described above, setting of attenuation correction similar to that shown in FIG. 12 can be performed.

Note that it is also possible that an adjustment key having the same function as the push and rotate key shown in the modification 1 (FIG. 8) is displayed on the display screen, and touch operations on the touch panel 19b are received as input operations corresponding to a push and a rotation of the push and rotate key.

As described above, the ultrasound diagnosis apparatus 1 according to the present embodiment is an ultrasound diagnosis apparatus 1 which causes the display 19a to display the ultrasound image 41 based on a received signal, received by the ultrasound probe 20, of ultrasound waves that are transmitted by the ultrasound probe 20 into a subject and reflected inside the subject, including: the hardware processor 100 which performs control of causing the display 19a to display the ultrasound image 41 subjected to attenuation correction, based on the received signal and setting of the attenuation correction, the attenuation correction correcting strength of the received signal lowered due to attenuation of the ultrasound waves inside the subject based on a gain (correction amount) according to a reflection depth of the ultrasound waves inside the subject; and the first rotation input key 51 and the second rotation input key 52 as an input receiver which receive an input operation that designates an adjustment amount related to the setting of the attenuation correction, wherein the hardware processor 100 changes the setting of the attenuation correction based on the adjustment amount designated by the input operation, and in the changing the setting of the attenuation correction, sets the correction amount for each of a plurality of the reflection depths that differ from each other, to an amount according to a product of the adjustment amount and a predetermined weighting factor, the predetermined weighting factor being set correspondingly to each of the plurality of reflection depths.

According to such a configuration, gains at the plurality of reflection depths can be changed at a time with weights according to the reflection depths, through simple input operations of rotating the first rotation input key 51 and the second rotation input key 52. By appropriately setting a weighting factor corresponding to each of the reflection depths, the sensitivity of a change in the gain at each of the plurality of reflection depths can be adjusted to desired sensitivity when the first rotation input key 51 and the second rotation input key 52 are rotated. Hence, according to the above-mentioned configuration, it is possible to more easily make desired setting of attenuation correction.

The hardware processor 100 sets the correction amount for the reflection depth in each of two or more adjacent ones of the plurality of depth segments D obtained by segmenting the ultrasound image 41 in a depth direction, based on weighting factor information In in which the weighting factors are set and associated with the plurality of depth segments D, respectively. Thus, gains in two or more depth segments D can be changed at a time with weights according to the reflection depths of the depth segments D, through simple input operations of rotating the first rotation input key 51 and the second rotation input key 52. Accordingly, in comparison with conventional technologies that adjust a gain in each depth segment D by using different slide switches or the like, it is possible to more easily make desired setting of attenuation correction.

The input receiver includes the first rotation input key 51 and the second rotation input key 52, each of which individually receives the input operation that designates the adjustment amount, and the hardware processor 100 sets the correction amount based on the weighting factor information In corresponding to one of the rotation input keys that receives the input operation, among sets of the weighting factor information In that differ from each other and are associated with the first rotation input key 51 and the second rotation input key 52, respectively. Thus, gains in the plurality of depth segments D can be changed at a time by using each of the first rotation input key 51 and the second rotation input key 52, to render different gain distributions. Accordingly, it is possible to more flexibly adjust a gain in each of the depth segments D.

The input receiver includes: the first rotation input key 51 (first input operation receiver) associated with first weighting factor information In, in which the weighing factor corresponding to the depth segment D1 (first depth segment) is set to be largest, and the second rotation input key 52 (second input operation receiver) associated with second weighting factor information In, in which the weighing factor corresponding to the depth segment D8 (second depth segment) that is deeper than the depth segment D1 is set to be largest. Thus, gains mainly in depth segments D with smaller reflection depths can be changed at a time by using the first rotation input key 51, and gains mainly in depth segments D with greater reflection depths can be changed at a time by using the second rotation input key 52.

In the ultrasound diagnosis apparatus 1 according to the modification 2, the input receiver further includes the third rotation input key 53 (third input operation receiver) associated with third weighting factor information In, in which the weighting factors corresponding to the depth segments D4 and D5 (third depth segment) that are deeper than the depth segment D1 and shallower than the depth segment D8 are set to be largest. Thus, gains mainly in depth segments D corresponding to middle reflection depths can be changed at a time by using the third rotation input key 53. Accordingly, it is possible to more flexibly adjust a gain in each of the depth segments D.

In the ultrasound diagnosis apparatus 1 according to modification 3, the input receiver includes the rotation input keys 541 to 548 that correspond to the depth segments D1 to D8, respectively, and in the weighting factor information In associated with each of the rotation input keys 541 to 548, a largest weighting factor is associated with the depth segment D corresponding to each rotation input key. Thus, while a gain in a target depth segment D is mainly adjusted, gains in a plurality of depth segments D adjacent to the target depth segment D can also be adjusted conjunctionally. Accordingly, it is possible to more easily and more flexibly make desired setting of the attenuation correction.

In the ultrasound diagnosis apparatus 1 according to the modification 1, the rotation input key 50 as the input receiver operates in a plurality of input modes, in each of which the rotation input key 50 receives the input operation that designates the adjustment amount, and receives a push operation (input mode designation operation) that designates any one of the plurality of input modes and a rotation operation (input operation) that designates the adjustment amount in the designated input mode, and the hardware processor 100 sets the correction amount based on the weighting factor information In corresponding to the input mode in which the input operation is received, among sets of the weighting factor information In that differ from each other and are associated with the plurality of input modes, respectively. Thus, gains in the plurality of depth segments D can be changed according to an input operation in each of the input modes, to render different gain distributions. Accordingly, it is possible to more flexibly adjust a gain in each of the depth segments D.

The rotation input key 50 is configured as a push and rotate key which receives the input mode designation operation depending on a pushed amount, and receives the input operation depending on a rotated amount, whereby it is possible to receive both of the input mode designation operation and the input operation by using a single operation key. Thus, since the number of operation keys of the operation input 18 can be reduced, it is possible to downsize the operation input 18 and to achieve lower cost.

The hardware processor 100 causes the display 19*a* to display the plurality of slider bars 42 that correspond to the plurality of depth segments D, respectively, and show the correction amount in each of the plurality of depth segments D, respectively, and when the input operation is carried out, changes the plurality of slider bars 42 to have contents indicating correction amounts set according to the input operation. Thus, it is possible to easily and visually grasp the contents of at-a-time changes in gains made through the input operations on the first rotation input key 51 and the second rotation input key 52.

When an operation is carried out on any of the plurality of slider bars 42 on the display 19*a*, the hardware processor 100 changes the correction amount in the depth segment D corresponding to the slider bar 42 on which the operation is carried out, according to the operation. Thus, it is possible to easily make fine adjustment to each of gains after at-a-time changes made through the input operations on the first rotation input key 51 and the second rotation input key 52, for each depth segment D.

The hardware processor 100 changes the setting of the attenuation correction, based on the weighting factor information In corresponding to one of depth settings of the ultrasound image 41 to be displayed, among a plurality of sets of the weighting factor information In that are generated beforehand correspondingly to the depth settings of the ultrasound image 41, respectively. Thus, gains in the plurality of depth segments D can be changed at a time with optimal weights for the depth setting of the ultrasound image 41. For example, when depth settings are changed, gain settings in a same diagnosis area of a subject can avoid greatly varying. It is possible to adjust a gain in a diagnosis site to a desired state through an intuitional input operation.

The hardware processor 100 changes the setting of the attenuation correction, based on the weighting factor information In corresponding to a type of the ultrasound probe 20 currently used, among a plurality of sets of the weighting factor information In that are generated beforehand correspondingly to a plurality of the ultrasound probes 20 of different types, respectively. Thus, gains in the plurality of depth segments D can be changed at a time with optimal weights for the ultrasound probe 20 currently used.

The hardware processor 100 changes the setting of the attenuation correction, based on the weighting factor information In corresponding to a diagnosis site to be diagnosed, among a plurality of sets of the weighting factor information In that are generated beforehand correspondingly to a plurality of different diagnosis sites of a subject, respectively. Thus, gains in the plurality of depth segments D can be changed at a time with optimal weights for the diagnosis site to be diagnosed.

In the ultrasound diagnosis apparatus 1 according to modification 4, the hardware processor 100 causes the display 19*a* to display a first slider bar 441 and a second slider bar 442 (operation object images) that represent objects of the input operation, and the input receiver receives an operation carried out on any of the first slider bar 441 and the second slider bar 442 on the display 19*a* as the input operation. Thus, it is possible to easily make the above-mentioned setting of the attenuation correction without averting a line of vision from the display 19*a*.

Moreover, the HDD 113 as a non-transitory computer readable storage medium in the above-described embodiment stores a program causing the hardware processor 100 (computer) provided to the ultrasound diagnosis apparatus 1, to perform: control to cause the display 19*a* to display the ultrasound image 41 subjected to attenuation correction, based on a received signal and setting of the attenuation correction, the attenuation correction correcting strength of the received signal lowered due to attenuation of ultrasound waves inside a subject based on a gain (correction amount) corresponding to a reflection depth of the ultrasound waves inside the subject; changing the setting of the attenuation correction based on an adjustment amount related to the setting of the attenuation correction, the adjustment amount being designated by an input operation carried out on an input receiver; and in the changing the setting of the attenuation correction, setting the correction amount, for each of a plurality of the reflection depths that differ from each other, to an amount according to a product of the adjustment amount and a predetermined weighting factor, the predetermined weighting factor being set correspondingly to each of the plurality of reflection depths. With the program causing the ultrasound diagnosis apparatus 1 to operate as described above, it is possible to more simply make desired setting of the attenuation correction.

A method for setting of attenuation correction in the above-described embodiment is a method for setting of attenuation correction in the ultrasound diagnosis apparatus 1, including: causing the display 19a to display the ultrasound image 41 subjected to attenuation correction, based on a received signal and setting of the attenuation correction, the attenuation correction correcting strength of the received signal lowered due to attenuation of ultrasound waves inside a subject based on a gain (correction amount) corresponding to a reflection depth of the ultrasound waves inside the subject; changing the setting of the attenuation correction based on an adjustment amount related to the setting of the attenuation correction, the adjustment amount being designated by an input operation carried out on an input receiver; and in the changing the setting of the attenuation correction, setting the correction amount, for each of a plurality of the reflection depths that differ from each other, to an amount according to a product of the adjustment amount and a predetermined weighting factor, the predetermined weighting factor being set correspondingly to each of the plurality of reflection depths. According to the method as described above, it is possible to more simply make desired setting of the attenuation correction.

Note that the present invention is not limited to the above-described embodiments and each modification, and various changes can be made.

For example, in the attenuation correction setting screen shown in FIG. 3 or the like, display of the ultrasound image 41 and the gain distribution image 43 may be omitted.

In the above-described embodiments and each modification, a description is given by using examples in which a plurality of input operation receivers (the first rotation input key 51 and the like) for changing gains across a plurality of depth segments D at a time are provided. However, the number of such input operation receivers may be one.

The slider bars 42a to 42h for individually adjusting a gain in each depth segment D may be provided as physical operation parts (slide switches) of the operation input 18, in place of the aspect causing the display 19a to display the slider bars 42a to 42h as objects of a touch operation through the touch panel 19b.

Setting of attenuation correction may be performed by using only the input operation receivers for changing gain settings across the plurality of depth segments D at a time, without providing the slider bars 42a to 42h.

Operations on the above-mentioned operation object images may be carried out on the screen through a pointer or the like, responding to an input operation on input receivers such as a mouse and a track ball, in place of the aspect in which operations are carried out on operation object images such as the slider bars 42 and 441 to 443 through a touch on the touch panel 19b.

In the above-described embodiments and each modification, a description is given by using examples in which the present invention is applied to the ultrasound diagnosis apparatus 1 including the operation display 19 and the ultrasound probe 20. However, the present invention is not limited to these examples. The present invention may be applied to an ultrasound diagnosis apparatus including the ultrasound diagnosis apparatus main body 10 with a configuration in which one or both of the operation display 19 and the ultrasound probe 20 are attachable to and detachable from the ultrasound diagnosis apparatus main body 10.

Although embodiments of the present invention have been described, the scope of the present invention is not limited to the above-described embodiments and incorporates the scope of the inventions according to claims and the scope of equivalences thereof.

The entire disclosure of Japanese Patent Application No. 2018-006065, filed on Jan. 18, 2018, is incorporated herein by reference in its entirety.

What is claimed is:

1. An ultrasound diagnosis apparatus which causes a display to display an ultrasound image based on a received signal, received by an ultrasound probe, of ultrasound waves that are transmitted by the ultrasound probe into a subject and reflected inside the subject, comprising:
   a hardware processor which performs control of causing the display to display the ultrasound image subjected to attenuation correction, based on the received signal and setting of the attenuation correction, the ultrasound image being segmented in the depth direction into a plurality of depth segments according to a reflection depth of the ultrasound waves inside the subject;
   a first input operation receiver which receives one first input operation that designates a first adjustment amount related to the setting of the attenuation correction; and
   a second input operation receiver which receives one second input operation that designates a second adjustment amount related to the setting of the attenuation correction,
   wherein the hardware processor
   changes the setting of the attenuation correction in two or more depth segments of the plurality of depth segments based on the one first input operation and changes the setting of the attenuation correction in the two or more depth segments of the plurality of depth segments based on the one second input operation, and
   in the changing the setting of the attenuation correction in response to the one first input operation, sets different correction amounts for each of the two or more depth segments according to a product of the first adjustment amount and first predetermined weighting factors respectively corresponding to each of the two or more depth segments and being set for the first input operation receiver, and
   in the changing the setting of the attenuation correction in response to the one second input operation, sets different correction amounts for each of the two or more depth segments according to a product of the second adjustment amount and second predetermined weighting factors respectively corresponding to each of the two or more depth segments and being set for the second input operation receiver, the second predetermined weighting factors being different than the first predetermined weighting factors.

2. The ultrasound diagnosis apparatus according to claim 1, wherein:
   a weighting factor corresponding to a first depth segment is set to be largest in the first predetermined weighting factors, and a weighting factor corresponding to a second depth segment that is deeper than the first depth segment is set to be largest in the second predetermined weighting factors.

3. The ultrasound diagnosis apparatus according to claim 2, further comprising a third input operation receiver associated with third predetermined weighting factors, in which a weighting factor corresponding to a third depth segment that is deeper than the first depth segment and shallower than the second depth segment is set to be largest.

4. The ultrasound diagnosis apparatus according to claim 1, wherein the first input operation receiver and the second input operation receiver operate in a plurality of input modes, and
the hardware processor sets the correction amount based on weighting factor information corresponding to the input mode in which the first input operation and the second input operation is received, among sets of the weighting factor information that differ from each other and are associated with the plurality of input modes, respectively.

5. The ultrasound diagnosis apparatus according to claim 4, wherein at least one of the first input operation receiver and the second input operation receiver includes a push and rotate key which receives the input mode designation operation depending on a pushed amount, and receives the input operation depending on a rotated amount.

6. The ultrasound diagnosis apparatus according to claim 1, wherein the hardware processor causes the display to display a plurality of correction amount images that correspond to the plurality of depth segments, respectively, and that show the correction amount in each of the plurality of depth segments, respectively, and when the input operation is carried out, changes the plurality of correction amount images to have contents indicating correction amounts set according to the input operation.

7. The ultrasound diagnosis apparatus according to claim 6, wherein when an operation is carried out on any of the plurality of correction amount images on the display, the hardware processor changes the correction amount in one of the depth segments corresponding to the correction amount image on which the operation is carried out, according to the operation.

8. The ultrasound diagnosis apparatus according to claim 1, wherein the hardware processor changes the setting of the attenuation correction, based on predetermined weighting factors corresponding to a type of the ultrasound probe currently used, among a plurality of sets of the predetermined weighting factors that are generated beforehand correspondingly to a plurality of the ultrasound probes of different types, respectively.

9. The ultrasound diagnosis apparatus according to claim 1, wherein the hardware processor changes the setting of the attenuation correction, based on predetermined weighting factors corresponding to a diagnosis site to be diagnosed, among a plurality of sets of the predetermined weighting factors that are generated beforehand correspondingly to a plurality of different diagnosis sites of a subject, respectively.

10. The ultrasound diagnosis apparatus according to claim 1, wherein the hardware processor causes the display to display an operation object image that represents an object of the input operation, and
the input receiver receives an operation carried out on the operation object image on the display as the input operation.

11. A non-transitory computer readable storage medium storing a program causing a computer provided to an ultrasound diagnosis apparatus which causes a display to display an ultrasound image based on a received signal, received by an ultrasound probe, of ultrasound waves that are transmitted by the ultrasound probe into a subject and reflected inside the subject, to perform:
control of causing the display to display the ultrasound image subjected to attenuation correction, based on the received signal and setting of the attenuation correction, the ultrasound image being segmented in the depth direction into a plurality of depth segments according to a reflection depth of the ultrasound waves inside the subject;
changing the setting of the attenuation correction in two or more depth segments of the plurality of depth segments based on a adjustment amount designated by one first input operation carried out on a first input operation receiver changing the setting of the attenuation correction in the two or more depth segments of the plurality of depth segments based on a second adjustment amount designated by one second input operation carried out on a second input operation receiver; and
in the changing the setting of the attenuation in response to the first input operation, setting different correction amounts for each of the two or more depth segments according to a product of the first adjustment amount and first predetermined weighting factors respectively corresponding to each of the two or more depth segments and being set for the first input operation receiver, and
in the changing the setting of the attenuation in response to the second input operation, setting different correction amounts for each of the two or more depth segments according to a product of the second adjustment amount and second predetermined weighting factors respectively corresponding to each of the two or more depth segments and being set for the second input operation receiver, the second predetermined weighting factors being different than the first predetermined weighting factors.

12. A method for setting of attenuation correction in an ultrasound diagnosis apparatus which causes a display to display an ultrasound image based on a received signal, received by an ultrasound probe, of ultrasound waves that are transmitted by the ultrasound probe into a subject and reflected inside the subject, comprising:
causing the display to display the ultrasound image subjected to attenuation correction, based on the received signal and setting of the attenuation correction, the ultrasound image being segmented in the depth direction into a plurality of depth segments according to a reflection depth of the ultrasound waves inside the subject;
changing the setting of the attenuation correction in two or more depth segments of the plurality of depth segments based on a adjustment amount designated by one first input operation carried out on a first input operation receiver changing the setting of the attenuation correction in the two or more depth segments of the plurality of depth segments based on a second adjustment amount designated by one second input operation carried out on a second input operation receiver; and
in the changing the setting of the attenuation in response to the first input operation, setting different correction amounts for each of the two or more depth segments according to a product of the first adjustment amount and first predetermined weighting factors respectively corresponding to each of the two or more depth segments and being set for the first input operation receiver, and in the changing the setting of the attenuation in response to the second input operation, setting different correction amounts for each of the two or more depth segments according to a product of the second adjustment amount and second predetermined weighting factors respectively corresponding to each of the two or more depth segments and being set for the second input operation receiver, the second predetermined weighting factors being different than the first predetermined weighting factors.

13. The ultrasound diagnosis apparatus according to claim 1, wherein the predetermined weighting factor is different for the each of the plurality of reflection depths, whereby the adjustment amount produces a different correction amount for each of the plurality of the reflection depths based on a respective predetermined weighting factor associated with the each of the plurality of reflection depths.

\* \* \* \* \*